United States Patent [19]
Paul

[11] Patent Number: 5,267,966
[45] Date of Patent: Dec. 7, 1993

[54] HEMOSTASIS CANNULA AND METHOD OF MAKING A VALVE FOR SAME

[75] Inventor: Ram H. Paul, Bloomington, Ind.

[73] Assignee: Cook Incorporated, Bloomington, Ind.

[21] Appl. No.: 952,354

[22] Filed: Sep. 28, 1992

[51] Int. Cl.$^5$ .................................... A61M 5/178
[52] U.S. Cl. ............................ 604/167; 604/256; 137/849; 137/845
[58] Field of Search .......... 604/167, 256, 905, 271; 251/149.1, 149.7; 137/849, 223, 845, 844

[56] References Cited

U.S. PATENT DOCUMENTS

| | | | |
|---|---|---|---|
| 2,546,672 | 3/1951 | Le Clair | 251/149.1 |
| 3,853,127 | 12/1974 | Spademan | 128/214.4 |
| 3,977,403 | 8/1976 | Patel | 251/149.1 |
| 4,000,739 | 1/1977 | Stevens | 128/214.4 |
| 4,143,853 | 3/1979 | Abramson | 251/149 |
| 4,177,814 | 12/1979 | Knepshield et al. | 128/348 |
| 4,334,551 | 6/1982 | Pfister | 137/614.03 |
| 4,412,836 | 11/1983 | Brignola | 604/87 |
| 4,424,833 | 1/1984 | Spector et al. | 137/849 |
| 4,430,081 | 2/1984 | Timmermans | 604/256 |
| 4,434,810 | 3/1984 | Atkinson | 137/849 |
| 4,436,519 | 3/1984 | O'Neill | 604/175 |
| 4,475,548 | 10/1984 | Muto | 128/207.14 |
| 4,496,348 | 1/1985 | Genese et al. | 604/167 |
| 4,610,665 | 9/1986 | Matsumoto et al. | 604/167 |
| 4,610,674 | 9/1986 | Suzuki et al. | 604/282 |
| 4,626,245 | 12/1986 | Weinstein | 604/256 |
| 4,634,432 | 1/1987 | Kocak | 604/167 |
| 4,657,772 | 4/1987 | Kocak | 427/2 |
| 4,705,511 | 11/1987 | Kocak | 604/282 |
| 4,798,594 | 1/1989 | Hillstead | 604/167 |
| 4,895,565 | 1/1990 | Hillstead | 604/256 |
| 4,932,633 | 6/1990 | Johnson et al. | 604/256 |
| 4,946,133 | 8/1990 | Johnson et al. | 251/149.1 |
| 5,006,113 | 4/1991 | Fischer | 604/167 |
| 5,064,416 | 11/1991 | Newgard et al. | 604/167 |
| 5,080,654 | 1/1992 | Picha et al. | 604/167 |
| 5,106,054 | 4/1992 | Mollenauer et al. | 251/149.1 |
| 5,114,408 | 5/1992 | Fleischhaker et al. | 604/167 |
| 5,125,903 | 6/1992 | McLaughlin et al. | 604/167 |
| 5,147,305 | 9/1992 | Nakamura | 604/256 |
| 5,149,327 | 9/1992 | Oshiyama | 604/256 |
| 5,176,652 | 1/1993 | Littrell | 604/256 |

FOREIGN PATENT DOCUMENTS 9110459  7/1991  World Int. Prop. O. .......... 604/167

*Primary Examiner*—John G. Weiss
*Attorney, Agent, or Firm*—Woodard, Emhardt, Naughton, Moriarty & McNett

[57] ABSTRACT

A hemostasis cannula comprising a housing having a passage therethrough sized to receive a catheter and a valve body mounted in the passage. The valve body includes an opening in one side thereof which forms a seal around a catheter enclosed within the cannula. The opening includes a cylindrical recess and four tapered slits extending from the base of the recess to a point shaped opening at the other side of said valve body. The method of making the slits includes cutting them with a four sided pyramid shaped tool.

6 Claims, 5 Drawing Sheets

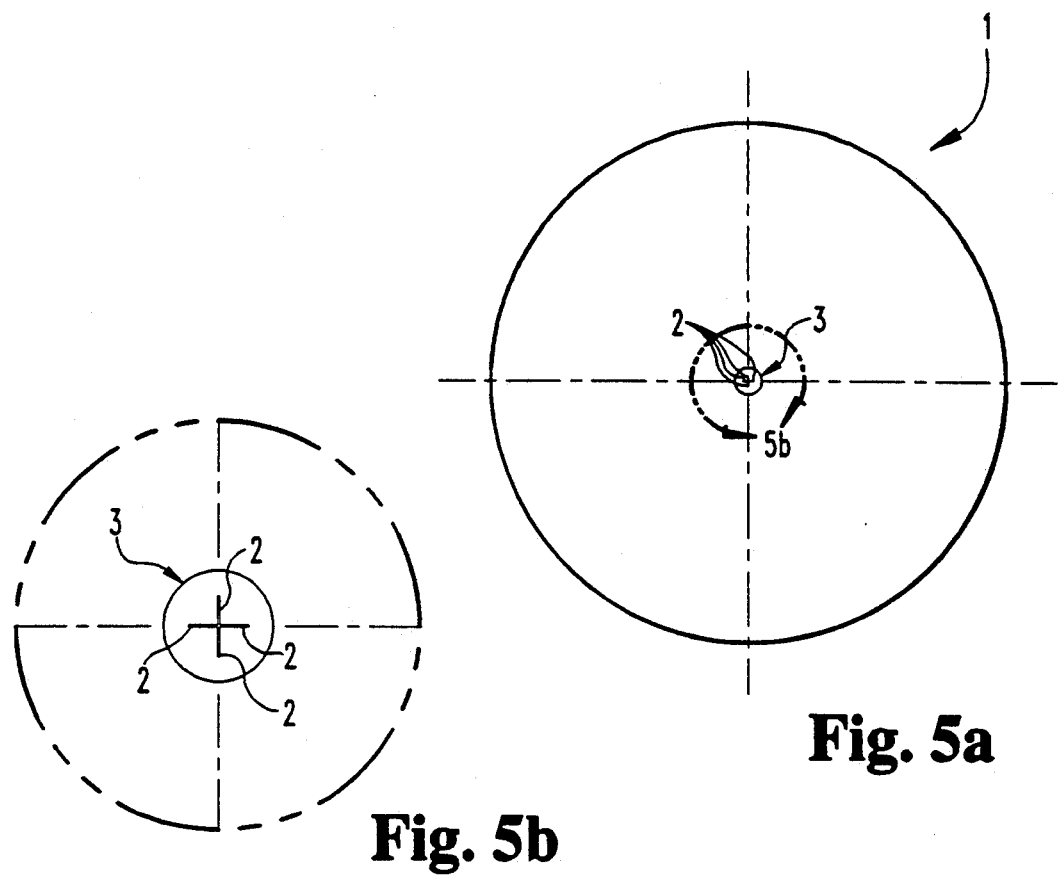
Fig. 5a
Fig. 5b
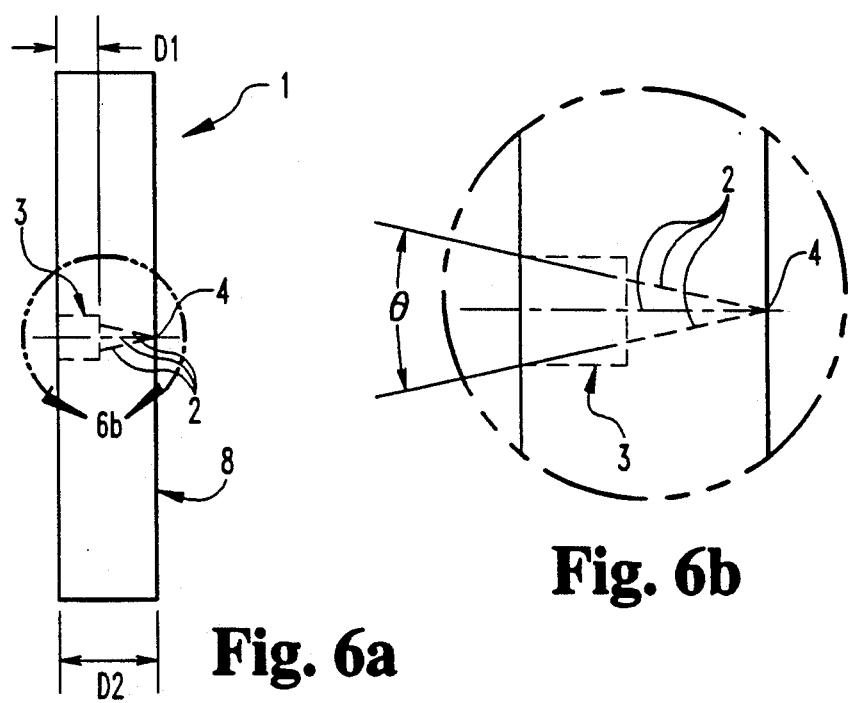
Fig. 6a
Fig. 6b

5,267,966

HEMOSTASIS CANNULA AND METHOD OF MAKING A VALVE FOR SAME

BACKGROUND OF THE INVENTION

This invention relates to a cannula or sheath and particularly to a cannula useful with angiographic catheters and to a method of making a valve for same.

In certain angiographic studies, the angiographer uses the Desilets-Hoffman procedure to do a multiple study. In this procedure, the angiographer obtains access to a patient's blood vessel by inserting a hollow needle through the skin and into the lumen of the blood vessel. A guide wire is passed through the needle and advanced through the artery or vein into the organ to be studied. The needle is removed leaving the guide wire in the organ. A cannula and dilator are advanced over the wire into the vessel and the dilator is removed along the guide wire. The angiographer then conducts the multiple studies by inserting various types of catheters into the vessel through the cannula or sheath. In order to avoid excessive bleeding and to insure against the possibility of an air embolism, this technique requires occlusion of the passage through the cannula during catheter changes.

One method of obtaining the required occlusion is to position a valve body formed from a pliable material in the passageway of the cannula. Such valve bodies are shown for instance in U.S. Pat. Nos. 4,000,739 to Stevens, 4,430,081 to Timmermans, 4,610,665 to Matsumoto et al. and 5,006,113 to Fischer. In each of these patents, one or more disk-like gaskets are mounted in the cannula passage. The disk-like gaskets or valve bodies include an opening therethrough which is biased to a closed position when no catheter is present in order to prevent an air embolism from occurring by air being drawn into the patient's vein through the cannula. When a catheter is inserted through the valve body into the passage of the cannula, the valve body conforms to the shape of the outer wall of the catheter, thereby preventing blood flow out of the cannula between the catheter and the valve body.

SUMMARY OF THE INVENTION

One embodiment of the present invention might include a hemostasis cannula comprising a housing having a passage sized to receive a catheter therethrough. A valve body formed from a single piece of pliable material is mounted in the passage of the housing. The valve body includes a cylindrical recess through one face which extends partly through the valve body and a plurality of tapering slits originating from the bottom surface of the cylindrical recess, continuing through the valve body and tapering to a small point shaped opening through the the second valve body face. The valve body is made of a resilient material which will conform to the shape of the outer wall of a catheter when the catheter penetrates through the slits and opening in the valve body thereby maintaining a fluid-tight seal between the outer wall of the catheter and the valve body. The resilient nature of the material causes the slits to close and the fluid-tight seal to be maintained when the catheter is withdrawn from the valve body.

One object of the present invention is to provide an improved hemostasis cannula.

Related objects and advantages of the present invention will be apparent from the following description.

BRIEF DESCRIPTION OF THE DRAWINGS

FIG. 5a is a front view of the valve body used in the hemostasis cannula of FIGS. 1 and 2.

FIG. 5b is an enlarged partially cut-away view of the valve body shown in FIG. 5a.

FIG. 6a is a side view of the valve body shown in FIGS. 5a and 5b.

FIG. 6b is an enlarged partially cut-away view of the valve body shown in FIG. 6a.

FIG. 7d is a cross-section of the distal tip of the 4-sided cutter taken along the line 7d—7d of FIG. 7a.

DESCRIPTION OF THE PREFERRED EMBODIMENT

Figure 1:
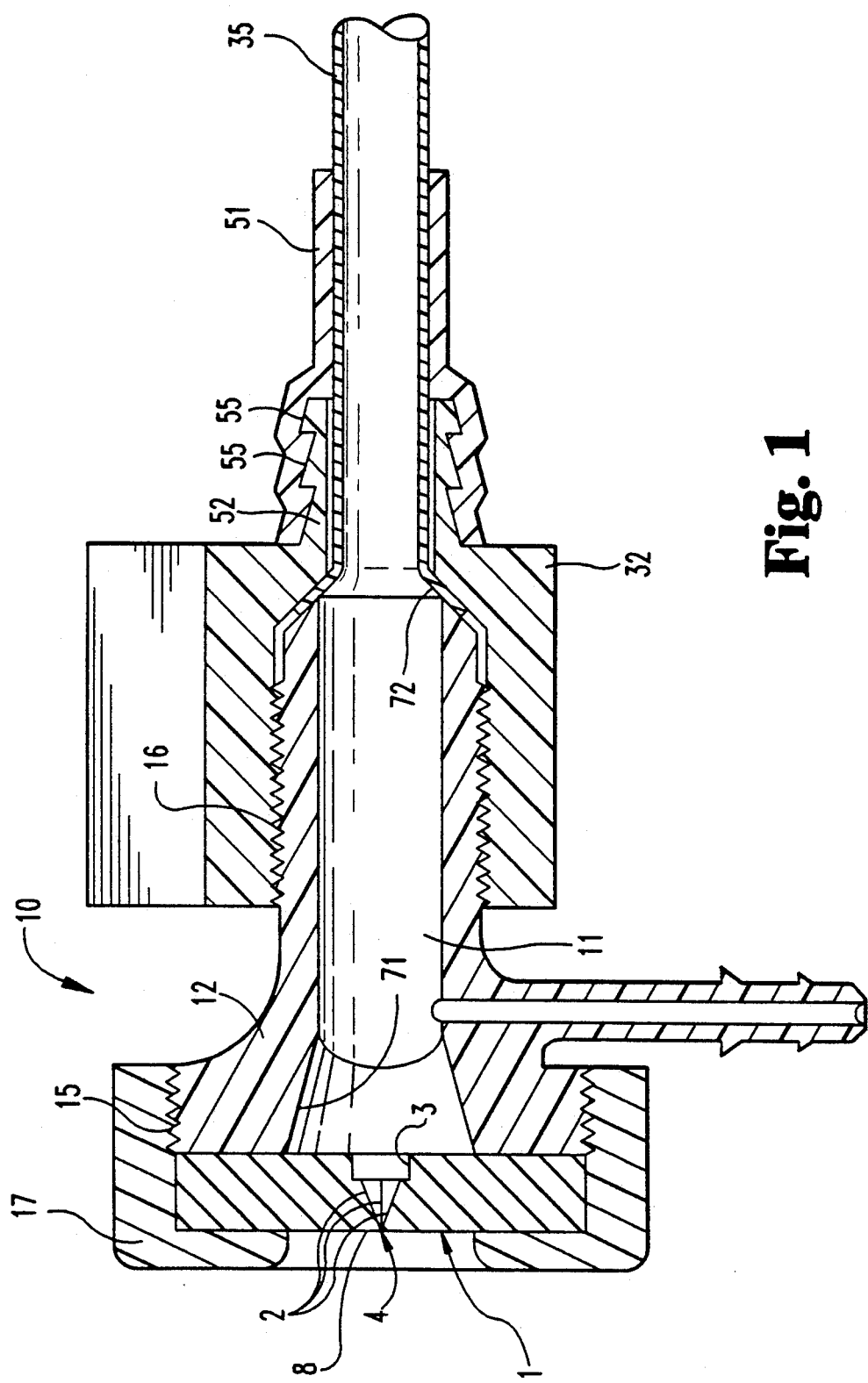
FIG. 1 is a cross-sectional view taken axially of a hemostasis cannula of the present invention.

For the purposes of promoting an understanding of the Principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
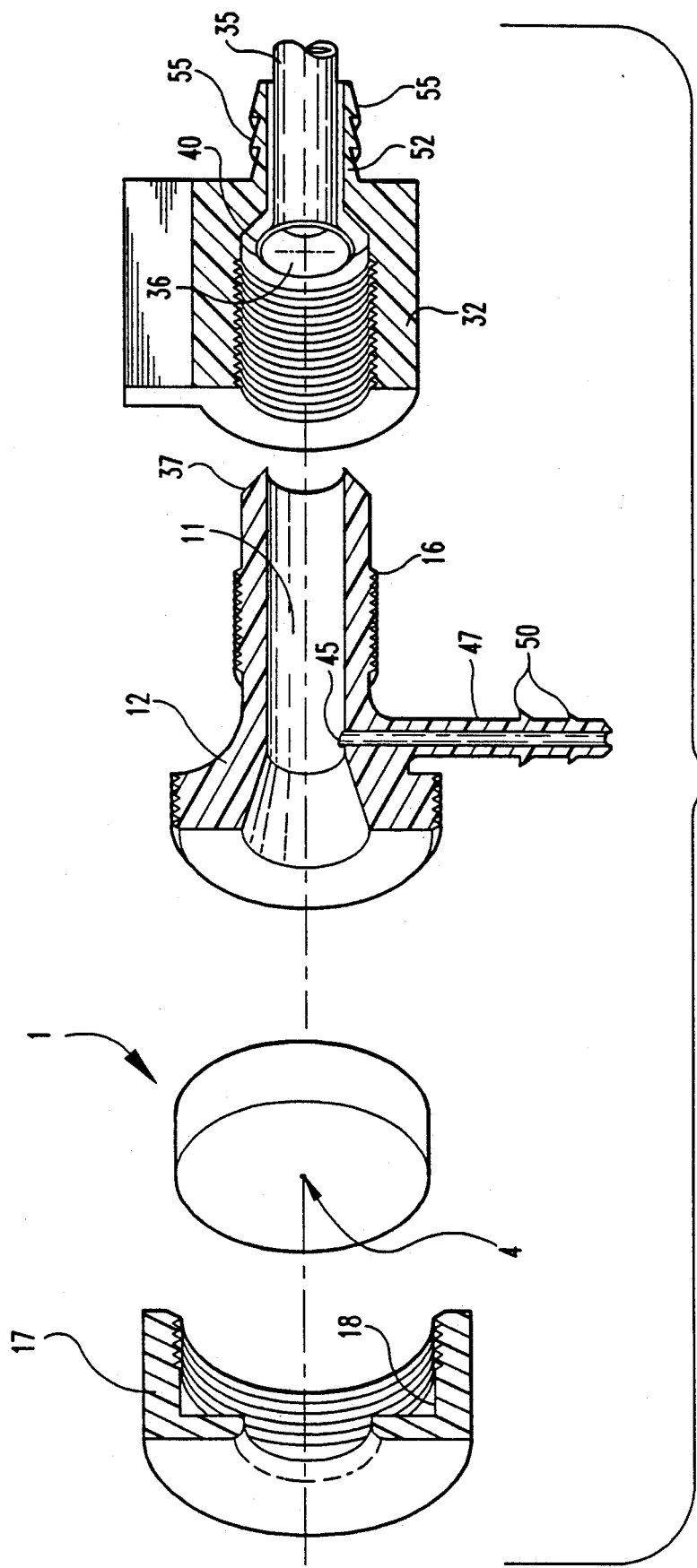
FIG. 2 is an exploded partially cut-away view of the embodiment of FIG. 1.

Referring now more particularly to the drawings, there is illustrated in FIGS. 1 and 2 a hemostasis cannula which includes a housing 10 having a passage 11 therethrough adapted to receive a catheter. Housing 10 is made up of a member 12 having two externally threaded surfaces 15 and 16. A cap 17, which includes housing recess 18, is threaded down on the member 12 on the threads 15 and is glued in place by a suitable cement or the like. Valve body 1 is received into housing recess 18 and is sandwiched between cap 17 and member 12.

The cannula housing 10 also includes an internally threaded member 32, the threads of which are suitable for mating engagement with the threads 16 on the member 12. The function of the member 32 is to receive and fix or hold the flexible tubing 35 to the housing 10. In the assembly procedure, adhesive or cement is placed on the flexible tubing 35 and between the members 12 and 32 for affixing the tubing and members together. The flexible tubing 35 has a flared end 36 which is fixed between the tapered surfaces 37 and 40 of the members 12 and 32.

Figure 3:
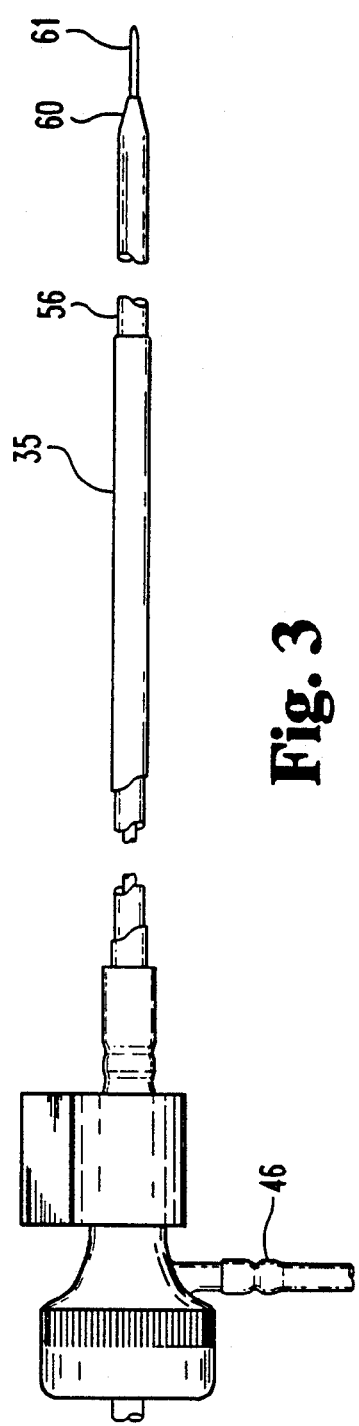
FIG. 3 is a side elevational view of the cannula having a dilator unit and wire guide therein.

Housing 10 is provided with a port 45 which communicates with passage 11 between valve body 1 and flexible tube 35 for introducing fluids into the patient's blood vessel. In order to ensure that blood does not flow out the flushing port 45, the physician normally maintains a positive pressure of flushing fluid through the flexible tubing 46 (FIGS. 3 and 4), which is attached to the projection 47 by means of the annular ridges 50. The flexible tubing 35 is further secured to housing 10 by means of shrinkable tubing 51 which is secured about collar 52 via the annular ridges 55. As seen in FIG. 3, a hollow plastic dilator 56 having an outer diameter substantially equal to that of catheter 57 (FIG. 4) may be positioned in the passage 11 with the tapered end 60 of the dilator extending past the distal end of tube 35. After the cannula has been inserted into the blood vessel over the guide wire 61 and the dilator 60, the dilator and guide wire may be removed and discarded.

Valve body 1 is cylindrical in shape and has a diameter dimension sufficient to cause the valve body 1 to fit snugly in housing recess 18. Additionally, the diameter dimension of the valve body 1 can be sufficient to cause a significant yet uniform compression of the valve body within the housing recess 18. A hole or cylindrical recess 3 is provided through one of the faces and extends partially through the valve body as shown in FIG. 1. The recess 3 may be formed by molding during the process of forming the disk or may be punched, cut or drilled in a separate operation. Additionally, as shown in FIGS. 1, 2, 5a and 5b, the valve body 1 includes four tapered slits 2 originating from the bottom of the cylindrical recess 3 and tapering to a small point shaped opening 4 through the opposite face of the valve body 1. In this way an opening is created completely through the valve body 1 for receiving a catheter or the like therethrough. Although the preferred embodiment for optimum longevity reasons includes four tapering slits radiating symmetrically from the central axis of the valve body 1. The use of four slits may not be required merely to function. Thus, one possible alternative is one planar slit originating from the bottom surface of the cylindrical recess 3 and tapering to a point shaped opening on the face 8 opposite that of the recess 3.

Valve body 1 is preferably made from silicon rubber or another elastomer preferably having a durometer hardness anywhere between 30 and 80 (A Range). FIG. 5a shows a front view of the valve body used in the hemostasis cannula of FIGS. 1 and 2. The valve body 1 is cylindrical in shape. In one specific embodiment of the invention, cylindrical recess 3 has a diameter of between 0.025 and 0.035 inches and has a depth of about 40% of the thickness of valve body 1. FIG. 5b is an enlarged partially cut-away view of the valve body shown in FIG. 5a. This view more clearly shows cylindrical recess 3 having four slits 2 that originate on the bottom surface of the recess 3. These slits 2 radiate symmetrically from a point at the center of the valve body 1 and each slit extends a distance less than the radius of the cylindrical recess 3.

FIG. 6a is a side view of the valve body shown in FIGS. 5a and 5b. In the one embodiment, the valve body 1 has a total thickness D2 of 0.065 inches and recess 3 has a depth D1 of 0.025 inches. FIG. 6b is an enlarged partially cut-away view of the valve body shown in FIG. 6a. This view more clearly illustrates the position of a four-sided bevel tool or cutter used in making the slits 2. It also shows the shape of the slits through the valve body 1. As shown in FIGS. 6a and 6b, the slits 2 originate at the bottom surface of the cylindrical recess 3 and taper at an angle Theta until they terminate at a point shaped opening 4 on the face 8 of the valve body 1. In the preferred embodiment, the blade tapering angle Theta is 30 degrees and this is also the tapering angle of the slits.

Figure 7A:
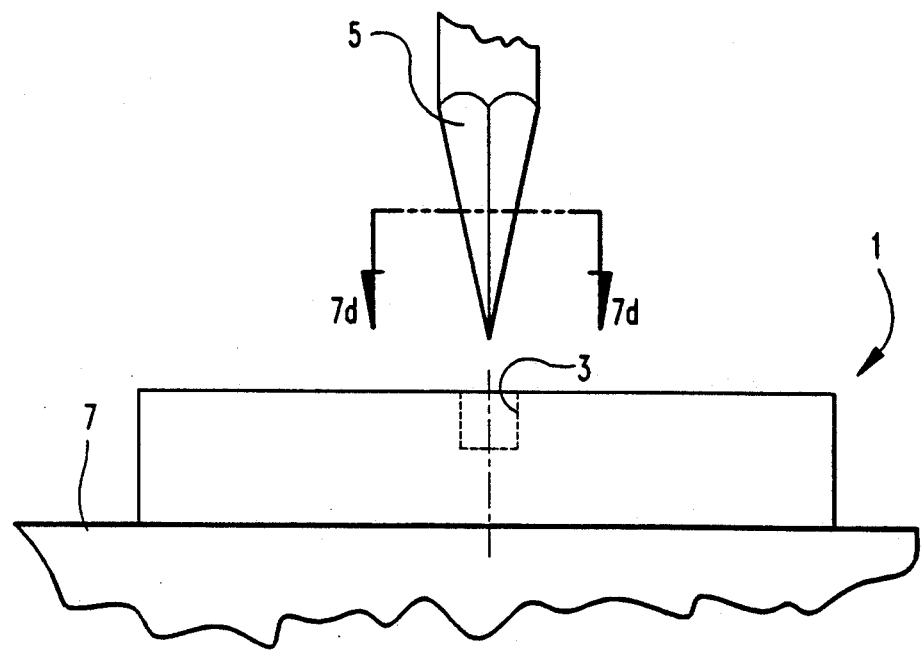
FIG. 7a is a side elevational view of the valve and a 4-sided cutter used to form slits originating from the cylindrical recess and tapering through the valve body.
Figure 7D:
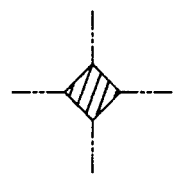
Figure 7B:
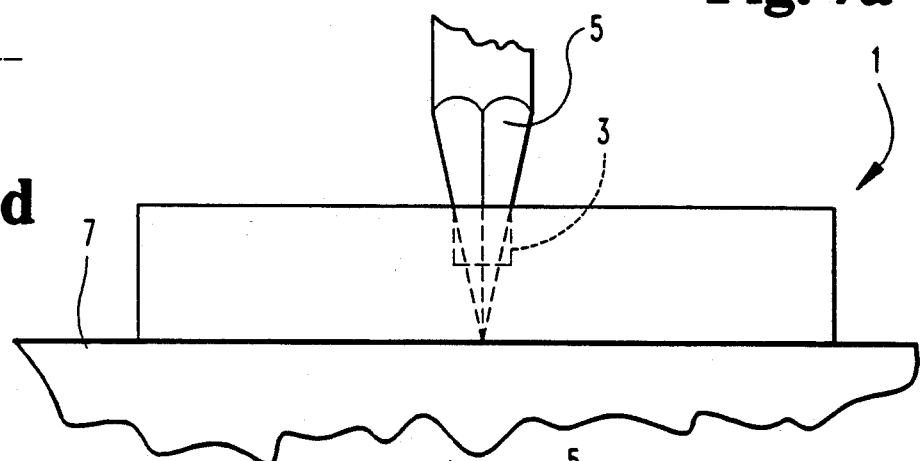
FIG. 7b is a side elevational view of the 4-sided cutter inserted into the cylindrical recess of the valve body and forming the tapered slits.
Figure 7C:
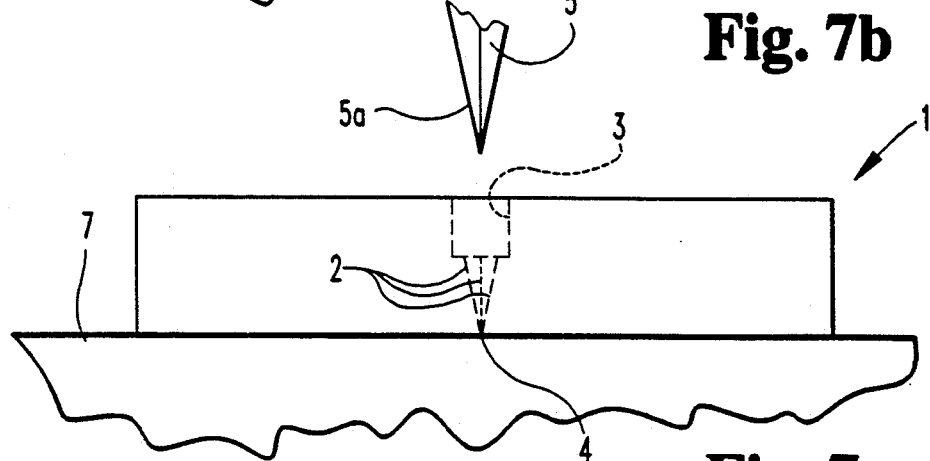
FIG. 7c is a side elevational view of the valve body having the four tapered slits after the 4-sided cutter has been removed.

Referring now to FIGS. 7a–7c, the method of making the valve body 1 is shown. Silicone disc 1 having a cylindrical recess 3 is shown resting on a block of fairly hard urethane, for example, 60 Durometers (D Range). FIG. 7a shows the four-sided or four-bladed cutter 5 used for forming the four tapered slits 2 in valve body 1 aligned above the cylindrical recess 3 of silicon disk. The four-sided cutter 5 has four sharp, tapered cutting edges 5a radiating symmetrically from a central axis through the cutter and coming together at a point at the distal end of the tool. The four-sided cutter 5 is forced through the cylindrical recess 3 of silicon disk 1 as shown in FIG. 7b. The tip of the four-sided cutter 5 abuts the urethane block 7 when the point has passed through the valve body 1. In this way urethane block 7 permits the cutter 5 to cut through the silicone, but only enough to complete the cut all the way through, thus limiting the exit opening to a point shaped opening 4 the size of the cutter tip. FIG. 7c shows the valve body 1 having the tapered slits 2 originating from the cylindrical recess 3 and terminating at a point shaped opening 4 on the face 8 of the valve body opposite the cutter's entry face.

Materials other than urethane can be used for the block 7. However, the block should be hard enough to stabilize the silicone disk, yet soft enough not to damage the point when it is forced through the disk.

FIG. 7d shows a cross-section of the four-sided cutter as being square and shows that the configuration of the cutter may be termed a pyramid with a relatively sharp apex angle of Theta or 30 degrees between the edges 5a that are opposite to each other.

Figure 4:
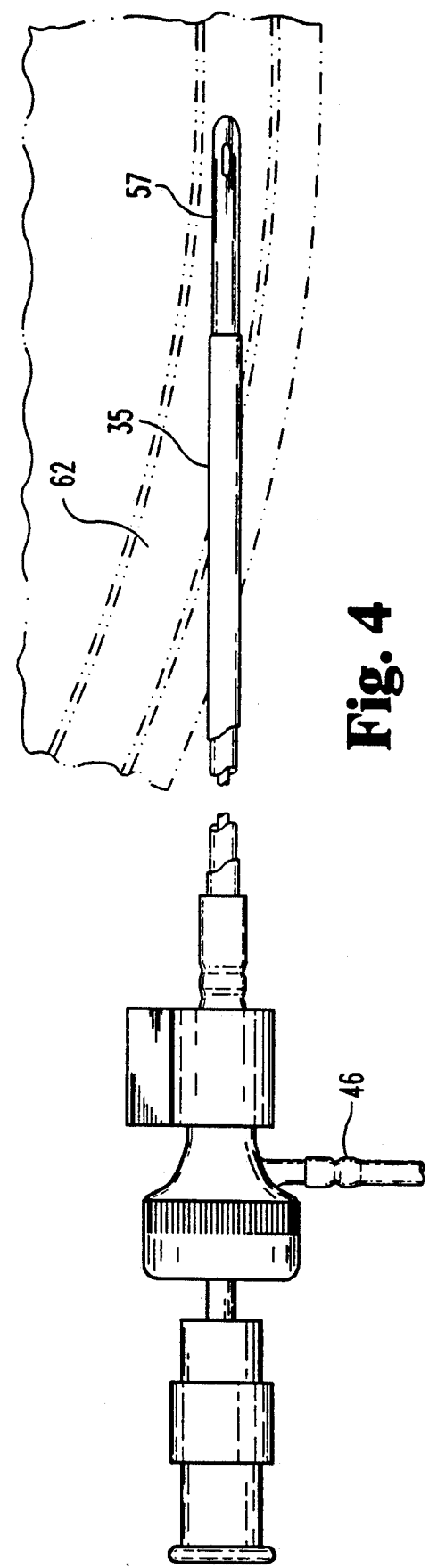
FIG. 4 is a view similar to FIG. 3 showing the cannula in position in the lumen of a blood vessel with a catheter enclosed therein.

In operation as shown in FIG. 4, a hollow needle subcutaneously enters the blood vessel. When the lumen 62 of the vessel has been penetrated, guide wire 61 is threaded into the needle an blood vessel, and the needle is removed. A hollow plastic dilator 60 is then passed through passage 11 of the cannula housing and is slid over guide 61. The physician then dilates the hole through the vessel wall by maneuvering the tapered end 60 of the dilator 56, and introduces the entrance tube 35 into vessel lumen 62. It should be noted that the outer diameter of the dilator at its constant diameter portion is close to the outer diameter of the flexible tubing 35 so that tubing 35 is guided through the wall of the vessel by the dilator. The cannula is then taped into position on the body of the patient. With the feed tube 46 fastened to projection 47, and while maintaining a slow flow of heparin saline solution into passage 11 through the tube 46, the physician withdraws dilator 56 and guide 61. At this point, tapered slits 2 in valve body 1 close. The closure of tapered slits 2 insures that no air passes through the opening 70 of cap 17 and through valve body 1 into passage 11. Thus, the present device not only prevents blood loss but also insures against the possibility of an air embolism.

The catheter 57 is then introduced through the opening in cap 17 and passes through valve body 1. Catheter 57 is guided through passage 11 and flexible tubing 35 by the tapered surfaces 71 and 72. The catheter finally passes into lumen 62 of the blood vessel. Cylindrical recess 3 and tapered slits 2 form a seal around the exterior wall of catheter 57 and prevent blood loss through hole 70 in the cap. Passage 11 is constantly flushed by a flow of heparin saline solution introduced through the port 45 and tubing 46 in order to prevent clotting. When catheter 57 has been maneuvered into position, radiopaque fluid is injected through the catheter and X-ray photographs may be taken of the radiopaque configuration of the organ being studied.

When multiple studies are indicated, or if a catheter has not been positioned correctly, the catheter may be easily removed from the cannula housing and replaced with another catheter. Also, a guide wire may be used by passing it through the cannula housing if needed. Because the slits 2 and opening 4 in valve body 1 close at the time of removal of the catheter, no bleeding is experienced by the patient and no air is allowed to enter into the patient's blood vessel in the event that the pressure external of the cannula is greater than the pressure within the blood vessel.

While the invention has been illustrated and described in detail in the drawings and foregoing description, the same is to be considered as illustrative and not restrictive in character. It is to be understood that only the preferred embodiments have been shown and described and that all changes and modifications that come within the spirit of the invention are desired to be protected.

What is claimed is:

1. A hemostasis cannula comprising:
   a housing having a passage sized to receive a catheter having an outer wall;
   a valve body formed from a single piece of pliable material and mounted in said passage of said housing, said valve body having a first face and a second face and a peripheral edge separating said faces, said valve body having a recess extending from said first face only partly through said valve body, said recess having a bottom surface, said valve body also including at least one tapered slit originating from said bottom surface of said recess and tapering to a point shaped opening at said second face, wherein said catheter enters said valve body through said point shaped opening;
   whereby said valve body will conform to said outer wall of said catheter when said catheter penetrates into said passage through said point shaped opening and through said at least one tapered slit and said opening of said valve body thereby maintaining a fluid tight seal between said outer wall of said catheter and said valve body.

2. The hemostasis cannula of claim 1 wherein said recess is a cylindrical recess.

3. The hemostasis cannula of claim 1 having four tapered slits originating from said bottom of said recess and terminating at a point shaped opening at said second face.

4. A hemostasis cannula comprising:
   a housing having a passage sized to receive a catheter having an outer wall;
   a valve body formed from a single piece of pliable material and mounted in said passage of said housing, said valve body having a first face and a second face and a peripheral edge separating said faces, said valve body having a point shaped openings at said second face, wherein said catheter enters said valve body through said point shaped opening, said valve body having a recess extending from said first face only partly through said valve body, said recess having a bottom surface, said valve body additionally including four tapered slits at 90 degrees to one another and tapering from said bottom surface of said recess to said point shaped hole;
   whereby said valve body will conform to said outer wall of said catheter when said catheter penetrates into said passage through said point shaped opening and through said at least one tapered slit and said opening of said valve body thereby maintaining a fluid tight seal between said outer wall of said catheter and said valve body.

5. The cannula of claim 4 wherein said slits have an apex angle of approximately 30 degrees.

6. A hemostasis cannula comprising:
   a housing having a passage sized to receive a catheter having an outer wall;
   a valve body formed from a single piece of pliable material and mounted in said passage of said housing, said valve body having a first face and a second face and a peripheral edge separating said faces, said first face including a cylindrical access extending only partly through said valve body, said recess having a bottom surface, said valve body additionally having a passage therethrough comprising four tapered slits originating from said bottom surface of said recess and terminating at a point shaped opening on said second face, wherein said catheter enters said valve body through said point shaped opening;
   whereby said valve body will conform to said outer wall of said catheter when said catheter penetrates into said passage through said point shaped opening and through said at least one tapered slit and said opening of said valve body thereby maintaining a fluid tight seal between said outer wall of said catheter and said valve body.

* * * * *

UNITED STATES PATENT AND TRADEMARK OFFICE
CERTIFICATE OF CORRECTION

PATENT NO. : 5,267,966
DATED : December 7, 1993
INVENTOR(S) : Ram H. Paul

It is certified that error appears in the above-indentified patent and that said Letters Patent is hereby corrected as shown below:

Column 6, line 36, please change "access" to --excess --.

Signed and Sealed this

Tenth Day of January, 1995

Attest:

BRUCE LEHMAN

Attesting Officer     Commissioner of Patents and Trademarks